United States Patent
Haupt et al.

[11] Patent Number: 5,932,079
[45] Date of Patent: Aug. 3, 1999

[54] ELECTROCHEMICAL MULTIGAS SENSOR

[75] Inventors: Stephan Haupt; Christoph Bernstein, both of Lübeck; Gero Sagasser, Bad Schwartau; Johannes Lagois, Lübeck, all of Germany

[73] Assignee: Drägerwerk AG, Lübeck, Germany

[21] Appl. No.: 08/987,206

[22] Filed: Dec. 9, 1997

[51] Int. Cl.⁶ .................................................. G01N 27/26
[52] U.S. Cl. .......................... 204/415; 204/412; 204/431; 204/432; 205/783; 205/785.5; 205/786; 205/786.5; 205/793; 205/794.5
[58] Field of Search .................................. 204/415, 431, 204/432, 412; 205/783, 785.5, 786, 786.5, 793, 794.5

[56] References Cited

U.S. PATENT DOCUMENTS

| | | | |
|---|---|---|---|
| 5,298,146 | 3/1994 | Braden et al. | 204/415 |
| 5,723,036 | 3/1998 | Chrzan et al. | 204/415 |

FOREIGN PATENT DOCUMENTS

| | | |
|---|---|---|
| 41 36 779 A1 | 5/1993 | Germany . |
| 42 31 256 A1 | 3/1994 | Germany . |

*Primary Examiner*—Bruce F. Bell
*Attorney, Agent, or Firm*—McGlew and Tuttle, P.C.

[57] ABSTRACT

An electrochemical measuring cell for the simultaneous detection of different gas components in a gas sample, with a plurality of measuring electrodes (4, 5, 6) behind a diffusion barrier (7), with a common reference electrode (8) and counterelectrode (9) in an acid electrolyte, and with a potentiostatic evaluating circuit. Improvements in terms of service life for a sensor for the simultaneous detection of oxygen and carbon monoxide is provided with a reference electrode formed of a sintered mixture of metal and its metal oxide, preferably from the platinum group, the iridium group or gold and the potential of the CO-measuring electrode (5) relative to the reference electrode (8) is set at about 0 to 300 mV, and that of the $O_2$-measuring electrode (4) is set at a value between −300 and −800 mV.

13 Claims, 1 Drawing Sheet

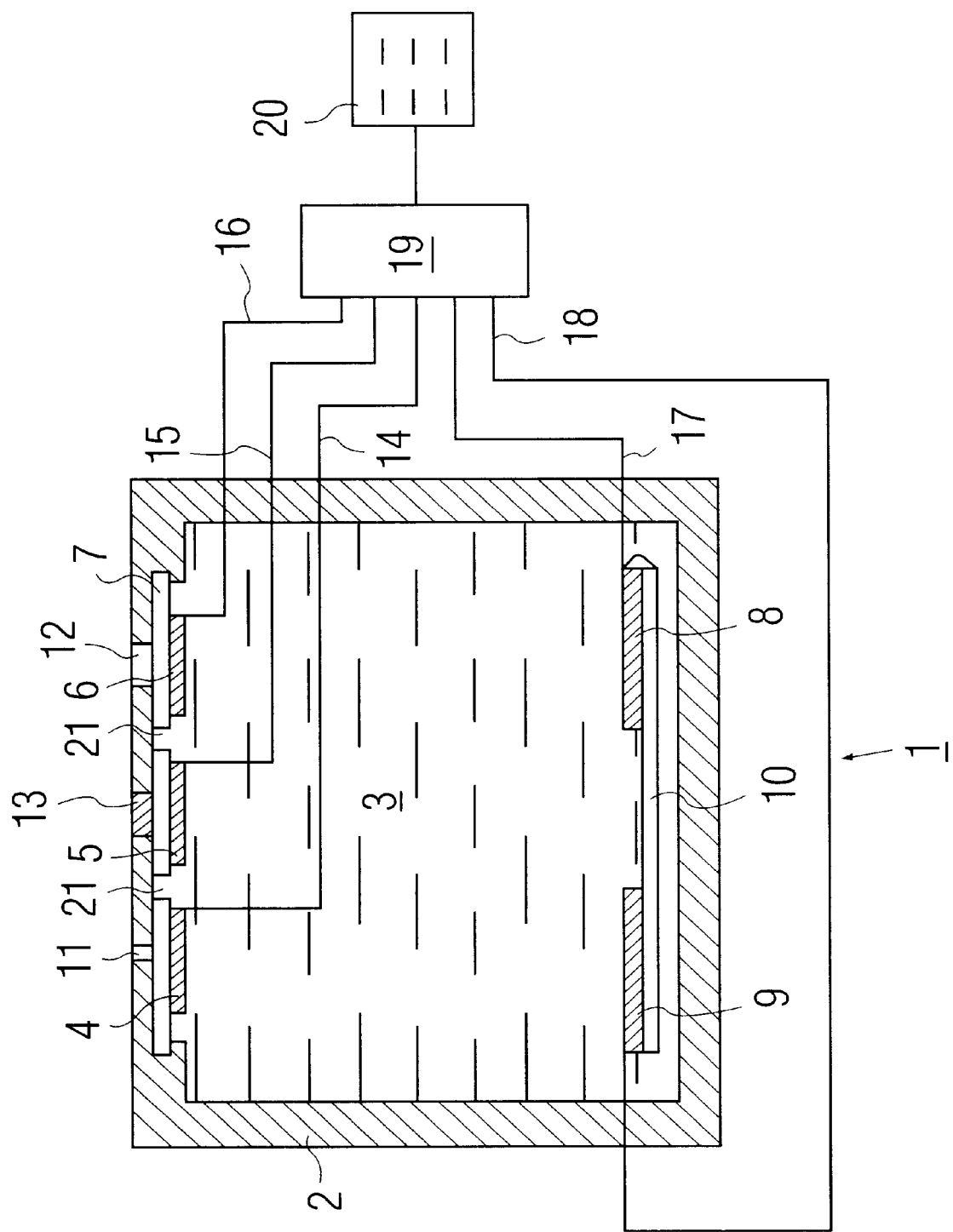

ELECTROCHEMICAL MULTIGAS SENSOR

FIELD OF THE INVENTION

The present invention pertains to an electrochemical measuring cell for the simultaneous detection of different gas components in a gas sample, with a plurality of measuring electrodes behind a diffusion barrier, with a common reference electrode, a counterelectrode in an acid electrolyte, and with a potentiostatic evaluating circuit, which maintains the potentials of the working electrodes at a predetermined value relative to the reference electrode independently from one another.

BACKGROUND OF THE INVENTION

An electrochemical measuring cell of his type has become known from DE 41 36 779 A1. Individual working electrodes in the form of spatially separated measuring fields are arranged on a surface of an electrolyte for the simultaneous detection of different gas components, while the common counterelectrode and the common reference electrode are arranged on the opposite side of the electrolyte. The electrodes are connected to a potentiostatic evaluating circuit, which contains individual control circuits, with which the potentials of the working electrodes relative to the reference electrode can be maintained at constant values individually and independently from one another.

Besides the analysis of toxic or combustible gases, the determination of the percentage of oxygen in the ambient atmosphere is also necessary in numerous measurement and monitoring tasks in the protection of people and at the workplace. Sensors for oxygen are based either on the galvanometric or the potentiometric principle of measurement, with the oxidation of a lead or silver anode. The maximum service life of such cells depends on the amount of anode material that can be reacted and the percentage of oxygen in the atmosphere to be monitored. The typical service life of such oxygen measuring cell is about up to 2 years.

Sensors for the analysis of toxic or combustible gases are frequently based on the amperometric principle of measurement, and their service life is usually longer than 2 years. The measuring cells must therefore be replaced at different times in measuring devices that are equipped with one measuring cell for $O_2$ measurement and another measuring cell for monitoring harmful gases.

An amperometric sensor for the measurement of the percentage of oxygen in the air, in which the reference electrode consists of a sintered mixture of metal and its metal oxide, as a result of which a long service life of the reference electrode and consequently of the entire sensor is obtained, has been known from DE 42 31 256. However, the prior-art gas sensor is suitable for the detection of one component only.

SUMMARY AND OBJECTS OF THE INVENTION

The primary object of the present invention is to provide an amperometric multigas measuring cell with long service life, with which harmful gases, especially carbon monoxide or hydrogen sulfide, can also be detected, besides oxygen.

According to the invention, an electrochemical measuring cell is provided for the simultaneous detection of different gas components in a gas sample. A plurality of measuring electrodes are provided behind a diffusion barrier, with a common reference electrode and a counterelectrode and an acid electrolyte. A potentiostatic evaluating circuit maintains the potentials of the working electrodes at a predetermined value relative to the reference electrode independently from one another. For the combined detection of CO and $O_2$, the reference electrode consists of a sintered mixture of metal and its metal oxide, preferably from the platinum group, the iridium group or gold. The potential of a CO-measuring electrode relative to the reference electrode is set at a value of about 0 mV to +300 mV and that of a $O_2$-measuring electrode is set at a value between −300 and −800 mV.

It was surprisingly found that an amperometric gas sensor with a reference electrode, which consists of a sintered mixture of metal and its metal oxide can also be used as a multigas sensor with long service life for the simultaneous detection of oxygen and carbon monoxide. The potentials of the measuring electrodes are set for this purpose relative to the reference electrode such that the potential of the $O_2$-measuring electrode is about −300 to −800 mV, and the potential for the CO-measuring electrode has a value of about 0 mV to +300 mV. The potentials set in the measuring cell according to the present invention represent a compromise between the sensitivity of the sensor and the cross selectivity to other gases.

According to another aspect of the invention, an electrochemical measuring cell is provided for the simultaneous detection of different gas components in a gas sample, with a plurality of measuring electrodes behind a diffusion barrier, with a common reference electrode and a counterelectrode in an acid electrolyte, and with a potentiostatic evaluating circuit. The potentiostatic evaluating circuit maintains the potentials of the working electrodes relative to the reference electrode at a certain value independently from one another. For the combined detection of $H_2S$ and $O_2$, said reference electrode is formed of a sintered mixture of metal and its metal oxide, preferably from the platinum group, the iridium group or gold. The potential of a $H_2S$-measuring electrode relative to the reference electrode is set at a value of about 0 to 200 mV, and that of an $O_2$-measuring electrode is set at a value between −300 mV and −800 mV; and the $H_2S$-measuring electrode consists of gold, iridium or carbon/graphite.

Such a sensor is suitable for the combined detection of oxygen and hydrogen sulfide. The potential of the $O_2$-measuring electrode relative to the reference electrode, which consists of a sintered mixture of metal and its metal oxide in this case as well, is set at a value between about −300 mV and −800 mV, and the potential of the $H_2S$-measuring electrode relative to the reference electrode is in the range of about 0 to 200 mV. The $H_2S$-measuring electrode preferably consists of gold, iridium or carbon or graphite.

Another embodiment of the present invention consists of integrating an $O_2$, CO and $H_2S$ measuring system in one measuring cell housing. This makes possible the especially inexpensive manufacture of the measuring cell according to the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic view of an electrochemical measuring cell.

DESCRIPTION OF THE PREFERRED EMBODIMENT

Referring to the drawing in particular, the only FIGURE schematically shows an electrochemical measuring cell 1 for the simultaneous detection of oxygen, carbon monoxide and hydrogen sulfide. The measuring cell 1 comprises a sensor housing 2, which surrounds an electrolyte space 3, which is filled with a suitable electrolyte, e.g., sulfuric acid; an $O_2$-measuring electrode 4; a CO-measuring electrode 5; an $H_2S$-measuring electrode 6; a diffusion barrier 7 limiting the access of gas to the electrodes 4, 5, 6; a reference electrode 8; and a counterelectrode 9. The reference electrode 8 and the counterelectrode 9 are arranged on a support membrane 10 made of PTFE. In the area of the electrodes 4, 6, the sensor housing 2 has perforations 11, 12, through which the gas to be analyzed has access to the diffusion barrier 7. A gas-selective filter 13, which lets only CO to the CO-measuring electrode 5, is located before the CO-measuring electrode 5. The electrodes 4, 5, 6, 8, 9 are connected via contact lines 14, 15, 16, 17, 18 to an evaluating circuit 19, which contains a potentiostat and processes the measured signals generated at the measuring electrodes 4, 5, 6. The measured values determined by the evaluating circuit 19 are displayed via a display unit 20.

The measuring electrodes 4, 5, 6 are arranged as segment-like metal layers on the side of the diffusion barrier facing the electrolyte space 3. The $O_2$-measuring electrode 4 and the CO-measuring electrode 5 consist of platinum, and the $H_2S$-measuring electrode 6 consists of iridium. No cross sensitivity develops at the $H_2S$-measuring electrode 6 to CO due to the use of iridium for the $H_2S$-measuring electrode 6 and due to the potential of about 150 mV set at the $H_2S$-measuring electrode 6. The potential of the $O_2$-measuring electrode 4 is set at a value between −300 and −800 mV, and that of the CO-measuring electrode 5 at a value of about 0 mV to 300 mV, both relative to the reference electrode 8. The reference electrode 8 consists of a sintered mixture of platinum and platinum oxide. Sulfuric acid is used as the electrolyte. For oxygen measurement, the measuring cell 1 operates according to the principle of the "oxygen pump," according to which the oxygen is pumped from the $O_2$-measuring electrode 4 to the counterelectrode 9.

To further improve the cross sensitivity of the CO measurement to hydrogen sulfide, a slot-like electrolyte barrier 21 is also provided within the diffusion barrier 7, next to the gas-selective filter 13, in order to prevent the cross diffusion of $H_2S$ to the CO-measuring electrode 5 within the diffusion barrier 7. A corresponding electrolyte barrier 21 is also located between the $O_2$-measuring electrode 4 and the CO-measuring electrode 5. In addition, the cross diffusion of oxygen within the diffusion barrier 7 from the perforation 12 or the filter 13 to the $O_2$-measuring electrode 4, which would lead to a measuring error at the $O_2$-measuring electrode 4, is prevented by the electrolyte barriers 21.

While specific embodiments of the invention have been shown and described in detail to illustrate the application of the principles of the invention, it will be understood that the invention may be embodied otherwise without departing from such principles.

What is claimed is:

1. An electrochemical measuring cell for the simultaneous detection of different gas components in a gas sample, the measuring head comprising:

a diffusion barrier;

a plurality of measuring electrodes behind said diffusion barrier;

a common reference electrode comprised of a sintered mixture of metal and its metal oxide;

a common counterelectrode;

an acid electrolyte, said common reference electrode and said common counterelectrode being in said acid electrolyte;

a potentiostatic evaluating circuit maintaining electric potentials of said measuring electrodes at a predetermined value relative to said reference electrode independently from one another for the combined detection of CO and $O_2$, wherein one of said measuring electrodes is a CO-measuring electrode with an electric potential relative to said reference electrode set at a value of about 0 mV to +300 mV; and one of said measuring electrodes is an $O_2$-measuring electrode with an electric potential set at a value between −300 and −800 mV.

2. The electrochemical measuring cell in accordance with claim 1, wherein said sintered mixture of metal and its metal oxide is from the platinum group, the iridium group or is gold.

3. The electrochemical measuring cell in accordance with claim 1, wherein one of said measuring electrodes is a $H_2S$-measuring electrode formed of gold, iridium or carbon/graphite, with an electrical potential relative to said reference electrode set at a value of about 0 to 200 mV; and further comprising cross sensitivity means for compensating for cross sensitivity.

4. The electrochemical measuring cell in accordance with claim 3, further comprising a gas-selective filter provided before said CO-measuring electrode as a means of compensating $H_2S$ at said CO-measuring electrode.

5. An electrochemical measuring cell for the simultaneous detection of different gas components in a gas sample, the measuring head comprising:

a diffusion barrier;

a plurality of measuring electrodes behind said diffusion barrier;

a common reference electrode comprised of a sintered mixture of metal and its metal oxide;

a common counterelectrode;

an acid electrolyte, said common reference electrode and said common counterelectrode being in said acid electrolyte;

a potentiostatic evaluating circuit maintaining electric potentials of said measuring electrodes at a predetermined value relative to said reference electrode independently from one another for the combined detection of $H_2S$ and $O_2$, one of said measuring electrodes being a $H_2S$-measuring electrode with an electric potential set relative to the said reference electrode at a value of about 0 to 200 mV, and another of said measuring electrodes is an $O_2$-measuring electrode with an electric potential set at a between −300 mV and −800 mV, said $H_2S$-measuring electrode being formed of gold, iridium or carbon/graphite.

6. The electrochemical measuring cell in accordance with claim 5, further comprising a gas-selective filter provided before said CO-measuring electrode as a means of compensating $H_2S$ at said CO-measuring electrode.

7. Electrochemical measuring cell in accordance with claim 5, wherein said cross sensitivity means is an electrolyte barrier within said diffusion barrier.

8. The electrochemical measuring cell in accordance with claim 5, wherein said sintered mixture of metal and its metal oxide is from the platinum group, the iridium group or is gold.

9. A method for simultaneous detection of gases in a sample, the method comprising;

providing a housing;

providing an acid electrolyte in said housing;

providing a diffusion barrier in said housing;

providing a CO measuring electrode in said electrolyte and against said diffusion barrier;

providing a $O_2$ measuring electrode in said electrolyte and against said diffusion barrier;

providing a common reference electrode in said electrolyte and formed of a sintered mixture of metal and metal oxide;

providing a common counterelectrode in said electrolyte;

setting an electric potential of said CO measuring electrode relative to said reference electrode to a value in a range of approximately 0 mV to +300 mV;

setting an electric potential of said $O_2$ measuring electrode relative to said reference electrode to a value in a range of approximately −300 mV to −800 mV wherein the detection of CO and $O_2$ in the sample are obtained.

10. A method in accordance with claim 9, wherein:

said metal of said reference electrode is formed from one of a platinum group, an iridium group and a gold group.

11. A method in accordance with claim 9, further comprising:

providing a $H_2S$ measuring electrode in said electrolyte and formed of one of gold, iridium and carbon graphite;

setting an electric potential of said $H_2S$ measuring electrode relative to said reference electrode to a value in a range of approximately 0 mV to +200 mV;

providing means for compensating $H_2S$ at said CO measuring electrode wherein detection of $H_2S$ in the sample is obtained.

12. A method for simultaneous detection of gases in a sample, the method comprising;

providing a housing;

providing an acid electrolyte in said housing;

providing a diffusion barrier in said housing;

providing a $H_2S$ measuring electrode in said electrolyte and against said diffusion barrier, said $H_2S$ measuring electrode being formed of one of gold, iridium and carbon/graphite;

providing a $O_2$ measuring electrode in said electrolyte;

providing a common reference electrode in said electrolyte formed of a sintered mixture of metal and metal oxide;

providing a common counterelectrode in said electrolyte;

setting an electric potential of said $H_2S$ measuring electrode relative to said reference electrode to a value in a range of approximately 0 mV to +200 mV;

setting an electric potential of said $O_2$ measuring electrode relative to said reference electrode to a value in a range of approximately −300 mV to −800 mV wherein the detection of $H_2S$ and $O_2$ in the sample are obtained.

13. A method in accordance with claim 12, wherein:

said metal of said reference electrode is formed from one of a platinum group, an iridium group and a gold group.

* * * * *